United States Patent
Cannon

[11] Patent Number: 5,558,635
[45] Date of Patent: Sep. 24, 1996

[54] EXCHANGEABLE GUIDE SYSTEM

[75] Inventor: Louis A. Cannon, Saginaw, Mich.

[73] Assignee: Medtronic, Inc., Minneapolis, Minn.

[21] Appl. No.: 349,949

[22] Filed: Dec. 6, 1994

[51] Int. Cl.$^6$ .................................................. A61M 31/00
[52] U.S. Cl. ........................... 604/49; 604/264; 604/164
[58] Field of Search .................................. 604/264, 280, 604/282, 164, 49, 52, 53, 95, 95; 128/656–658, 772

[56] References Cited

U.S. PATENT DOCUMENTS

| | | |
|---|---|---|
| 4,917,103 | 4/1990 | Gambale et al. . |
| 4,922,923 | 5/1990 | Gambale et al. . |
| 5,031,636 | 7/1991 | Gambale et al. . |
| 5,035,686 | 7/1991 | Crittenden et al. . |
| 5,120,323 | 6/1992 | Shockey et al. . |
| 5,163,903 | 11/1992 | Crittenden et al. . |
| 5,234,407 | 8/1993 | Teirstein et al. . |
| 5,281,203 | 1/1994 | Ressemann ............................. 604/164 |

*Primary Examiner*—John D. Yasko
*Attorney, Agent, or Firm*—John A. Artz; Dianne M. F. Plunkett; Harold R. Patton

[57] ABSTRACT

A system for exchanging a smaller guide catheter with a larger guide catheter without removal of the coronary guide wire during angioplasty. An extender guide catheter is connected to the end of the implanted guide catheter, such as with a connector member. A larger guide catheter is advanced over the extended and implanted guide catheters into the aorta and the latter guide catheters are removed.

22 Claims, 9 Drawing Sheets

EXCHANGEABLE GUIDE SYSTEM

TECHNICAL FIELD

This invention relates to catheter systems used in coronary angioplasty, and more particularly to a system for exchanging guide catheters without having to remove the angioplasty guide wire from the coronary artery.

BACKGROUND ART

In treating coronary artery disease, a variety of surgical techniques are employed to recanalize an occluded or partially occluded artery segment without requiring open heart surgery. Percutaneous transluminal angioplasty or related procedures have become commonly used in the treatment of various obstructive disorders of the human circulatory system. To date, these angioplasty and related procedures have been utilized to treat stenotic lesions of the coronary arteries, and other obstructive vascular lesions. In one technique, a catheter using an expandable balloon at its distal end is routed through the vascular system and ultimately into the coronary artery with the balloon being positioned at the stenotic lesion. Once positioned, the balloon is inflated to compress the plaque into the wall of the blood vessel, thus restoring circulation through the artery.

In general, the usual technique for performing angioplasty procedures requires the initial placement of an elongated flexible angio catheter known as a "guide catheter". The guide catheter is initially inserted into an appropriate artery, such as the femoral artery or axillary artery, and subsequently advanced transluminally to a point where the distal tip of the guide catheter is positioned within a target blood vessel, near the obstructive lesion to be treated. The guide catheters have an internal lumen sufficiently large to receive and pass balloon catheters, or other working catheters through them.

A flexible guide wire is inserted through the lumen of the guide catheter such that the distal end of the guide wire emerges out of and extends beyond the distal tip of the guide catheter. The guide wire is advanced under fluoroscopic guidance, to a point where the distal end of the wire has advanced fully through the stenotic lesion or obstruction to be treated. Thereafter, a small balloon catheter, imaging device or other device used to ameliorate coronary artery disease is inserted and advanced over the guide wire, through the lumen of the guide catheter, to a point adjacent the lesion or obstruction. At this point, the device is operated or the balloon is inflated one or more times to bring about the desired dilation of the offending lesion and/or distention of the surrounding blood vessel wall. After such treatment is completed, the balloon catheter (or other device), guide wire and guide catheter are withdrawn and removed from the patient.

Various types and sizes of guide catheters are available. Prior to the procedure, a guide catheter of appropriate type and size is preselected by the surgeon for each particular patient. However, sometimes a preselected guide catheter proves to be inadequate and it becomes necessary or desirable to exchange one guide catheter for another during the course of the angioplasty procedure. If the decision to change a guide catheter is reached prior to the insertion of the coronary guide wire, the guide catheter may simply be extracted and replaced before the guide wire is inserted without any substantial risk of complication. However, if, as often occurs, the decision to replace the guide catheter is not reached until after the guide wire has been fully inserted through the guide catheter and advanced through the stenotic lesion, an attempt to replace the guide catheter at that point is complicated by the need to maintain the previously inserted guide wire in its operative position, without accidentally pulling the guide wire back through the lesion.

Currently, interventional cardiologists must choose between large catheter systems and small catheter systems for guide catheter placement. The larger catheter systems allow more flexibility in terms of being able to place large perfusion balloons, atherectomy devices, or coronary stents. Systems using the smaller diameter catheters have several advantages, such as decreasing the risk of hemorrhaging around the groin area of the patient, decreasing patient morbidity, decreasing contrast usage, allowing quicker ambulation (potentially shortening the length of hospital stay), and reducing costs for the angioplasty procedure. There is hesitancy among some cardiologists, however, to use smaller guide catheter systems because of the difficulty in having to exchange to a large catheter system if it is necessary to do so during the surgical procedure.

SUMMARY OF THE INVENTION

It is an object of the present invention to provide a system and/or device to facilitate removal and replacement of a cardiovascular guide catheter when necessary or desirable to do so. It is a further object of the present invention to provide a method and system for exchanging guide catheters which allow the interventional cardiologist to initially use small profile systems without the need to remove the angioplasty wire or the entire system to put in a larger system.

These and other objects, features and advantages of the invention will become apparent from the following description of the invention when taken in combination with the enclosed drawings and appended claims.

The present invention provides an exchangeable guide catheter system which allows exchange of catheters quickly and efficiently. When a situation develops in which a larger catheter is required during coronary angioplasty, the existing guide catheter is extended with a guide catheter extender. A connector device, such as a threaded tube, is used to secure the guide catheter extender to the existing guide catheter. A larger introducer sheath is also exchanged for the existing smaller introducer sheath. Further, if the guide wire is not of sufficient length, it is extended in order to allow use of the extender catheter.

At this point, the larger guide catheter to be exchanged for the smaller guide catheter is inserted over the extender guide catheter and the existing guide catheter. Once the replacement guide catheter is placed in the appropriate position, or as it is being put into position, the original guide catheter together with the extender guide catheter are removed.

The guide catheter exchange system in accordance with the present invention allows the coronary guide wire to remain in position beyond the area of stenosis. Once the larger guide catheter is in position, larger perfusion balloons, atherectomy devices, coronary stents and the like can be used as needed.

A plug, wire turner, guide occluder or the like could be positioned at the proximal end of the guide catheter to occlude the smaller guide catheter and diminish the flow of blood and other fluids from the system during the exchange. A plug or occluder could also be positioned at the proximal end of the larger (replacement) guide catheter for the same reason. Further, the replacement introducer sheath can have a tapered distal end in order to provide a better seal with the smaller guide catheter prior to introduction of the exchanger guide catheter.

BRIEF DESCRIPTION OF THE DRAWINGS

FIG. 5A is an enlarged view depicting a split or dissection of the arterial wall;

DESCRIPTION OF THE PREFERRED EMBODIMENTS

Figure 1:
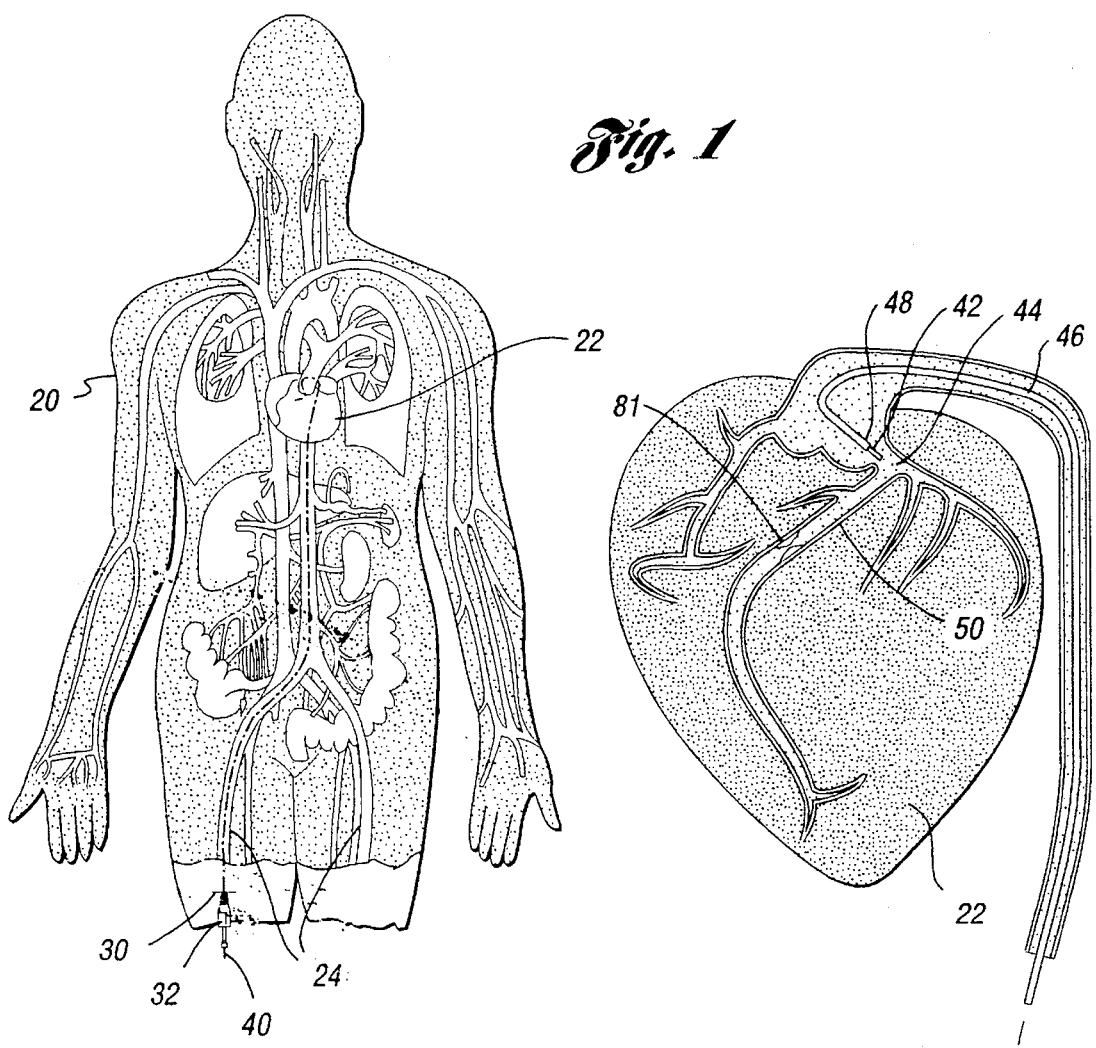
FIG. 1 illustrates a patient with the heart and vascular system highlighted.

Angioplasty procedures used to treat stenotic lesions of the coronary arteries and other obstructive vascular lesions, typically use inflatable balloons to restore circulation through the arteries. FIG. 1 depicts a patient 20 showing the various internal organs, including the heart 22 and femoral arteries 24. After the insertion site 30 adjacent the patient's groin area is localized and anesthetized, a percutaneous entry needle (not shown) is used to ease the entry of a guide wire, sheath and guide catheter system into the artery. First a catheter guide wire 40 is inserted into the artery 24 and routed into the patient's heart. This guide wire 40 is commonly referred to as the "larger" or "catheter" guide wire and typically has a diameter of 0.35"–0.38". Then, an introducer sheath 32 preferably with a one-way valve (diaphragm) 34 is inserted through the opening and into the artery 24 over the guide wire 40.

Figure 2:
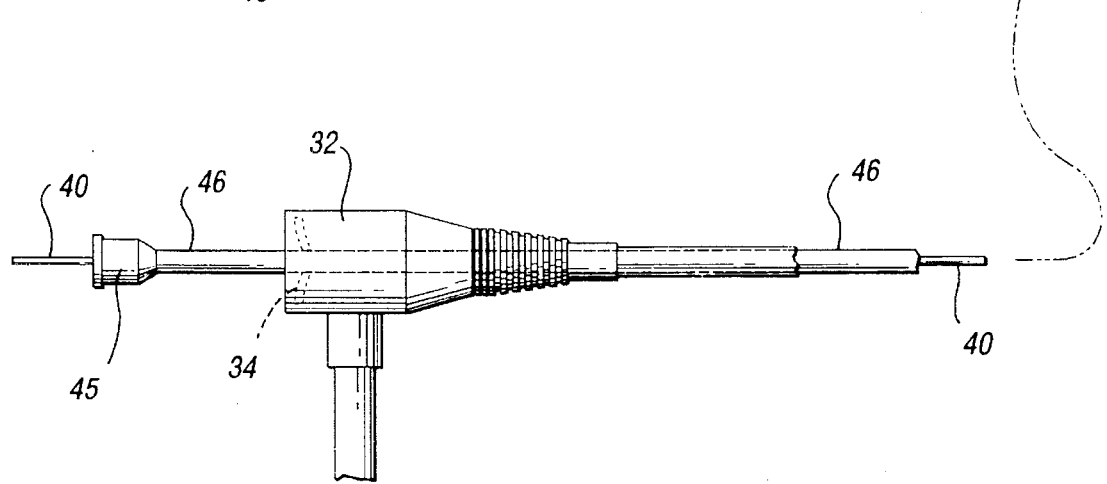
FIG. 2 illustrates the use of an introducer sheath, guide wire and guide catheter.

A guide catheter 46 is then slid over the catheter guide wire 40 and pushed along the wire until the distal end 48 is positioned adjacent the arch of the aorta 44 at the opening of the artery 50. This is shown in FIG. 2. The distal end of the guide catheter typically has a Judkins curve at its end in order to allow the guide catheter to be positioned in the appropriate position in the heart. As known, the guide catheter serves as a guide for the balloon catheter system and also facilitates the insertion of dye (a/k/a "contrast") into the coronary artery in order for the stenosis 81 to be viewed fluoroscopically.

Figure 3:
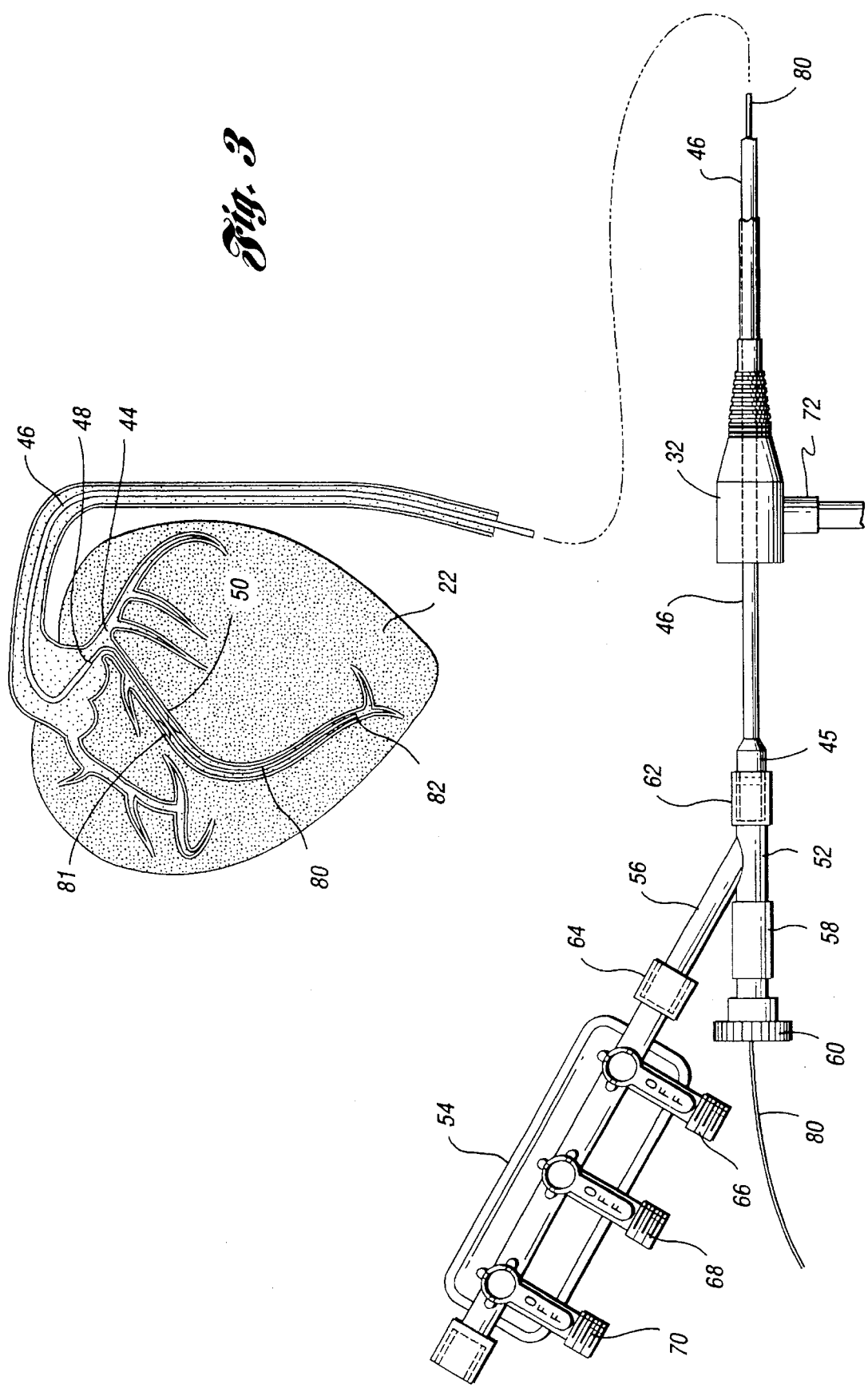
FIG. 3 illustrates the positioning of a coronary guide wire through and beyond the stenosis.

Once the guide catheter is placed in the appropriate position, the catheter guide wire is removed and a hub 52 and manifold 54 are secured to the end of the guide catheter. This is shown in FIG. 3. The hub 52 has a "Y" shape with a first passageway member 56 for connection to the manifold and a second passageway member 58 used to allow insertion of other instruments into the guide catheter 46. The hub 52 is connected to the luer fitting 45 on the guide catheter 46 by connector 62. The manifold 54 is connected to the hub 52 by connector 64. A "toohey" fitting 60 prevents blood and other fluids from leaking out of the end of passageway 58.

The manifold 54 preferably has at least three ports, one port 66 for attachment to the bottle of injection dye (contrast), another port 68 for connection to the pressurized fluid system, and the third port 70 for connection to a transducer to monitor blood pressure. It is also possible to have a side port 72 on the introducer sleeve 32 either to monitor the blood pressure or to draw blood for lab samples. Of course, lab samples can also be obtained from the guide catheter in conventional ways known in the art.

At this point, the guide catheter is adjusted to the optimum or desired position at the entrance to the artery with the blockage.

A flexible (or floppy) guide wire 80 is then inserted through the lumen of the guide catheter 46 until it extends slightly beyond the distal tip 48 of the guide catheter. The flexible guide wire is advanced under conventional fluoroscopic procedures to a point where the distal end 82 of the wire has passed completely through the stenosis 81 or obstruction to be treated. Preferably, the end of the wire 80 is positioned a sufficient distance past the stenosis, as shown in FIG. 3. This guide wire 80 is typically referred to as the "smaller", "coronary" or "flexible" guide wire and typically has a diameter of 0.014"–0.018".

Figure 4:
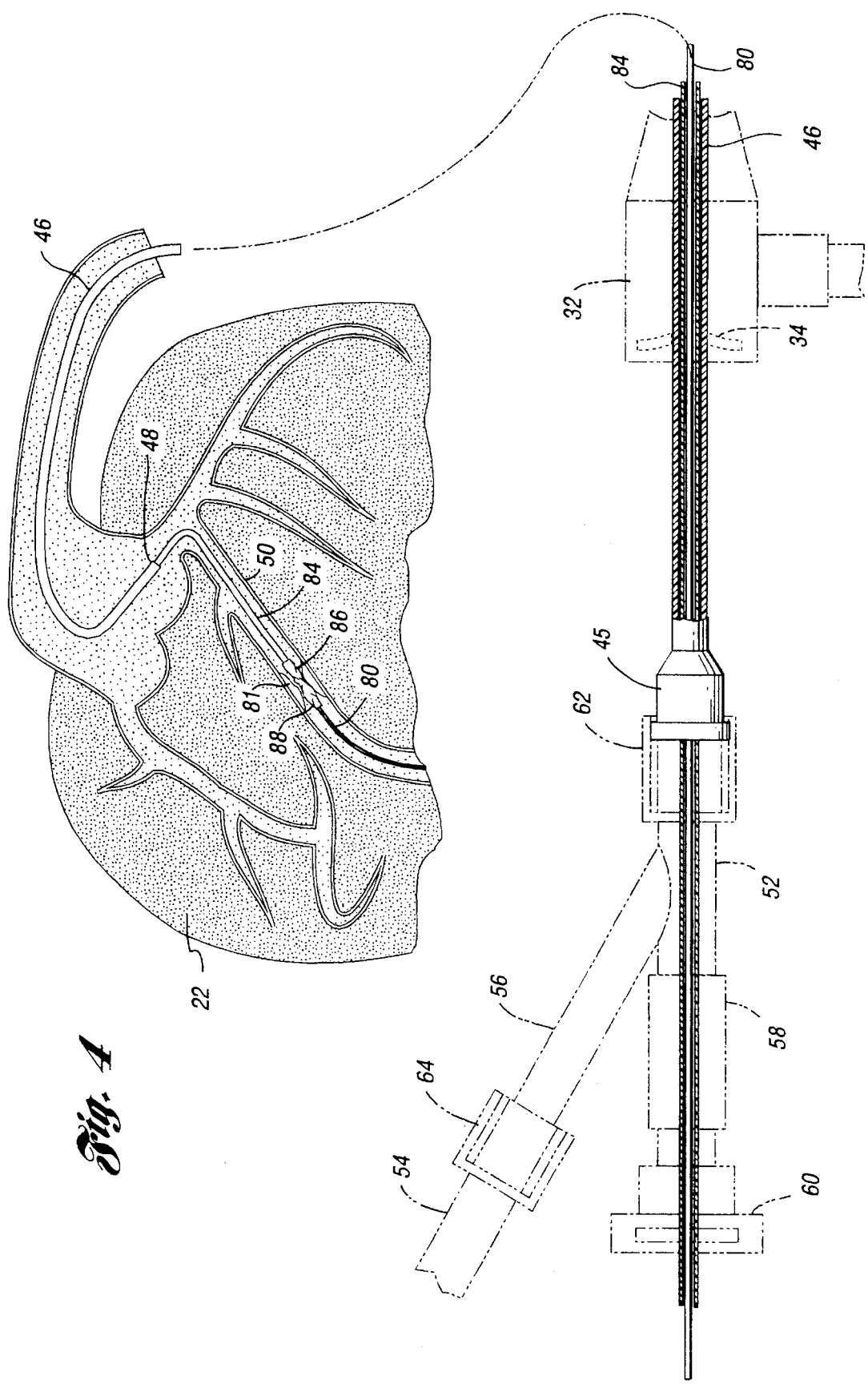
FIG. 4 illustrates the positioning of a balloon catheter.

Thereafter, as shown in FIG. 4, a small balloon catheter 84 is inserted and advanced over the guide wire. (As known in the art, it is also possible to use other devices to dilate or remove the plaque blockage; the balloon catheter is described herein as a preferred and representative system.) The balloon catheter 84 has a small inflatable balloon 86 adjacent its distal end 88. The balloon catheter is advanced through the lumen of the guide catheter, until the balloon is positioned at the site of the lesion or obstruction. It is also possible to insert the smaller guide wire 80 and balloon catheter 84 together inside the guide catheter 46 for ease of installation. The guide wire 80 is first threaded through the lumen of the balloon catheter 84 and the two items are then pushed through the guide catheter 46 until they almost emerge from the distal end 48 of the guide catheter. The guide wire 80 is first pushed past the stenosis 81 and then the balloon catheter 84 is advanced until the balloon 86 is properly positioned at the stenosis.

Figure 5:
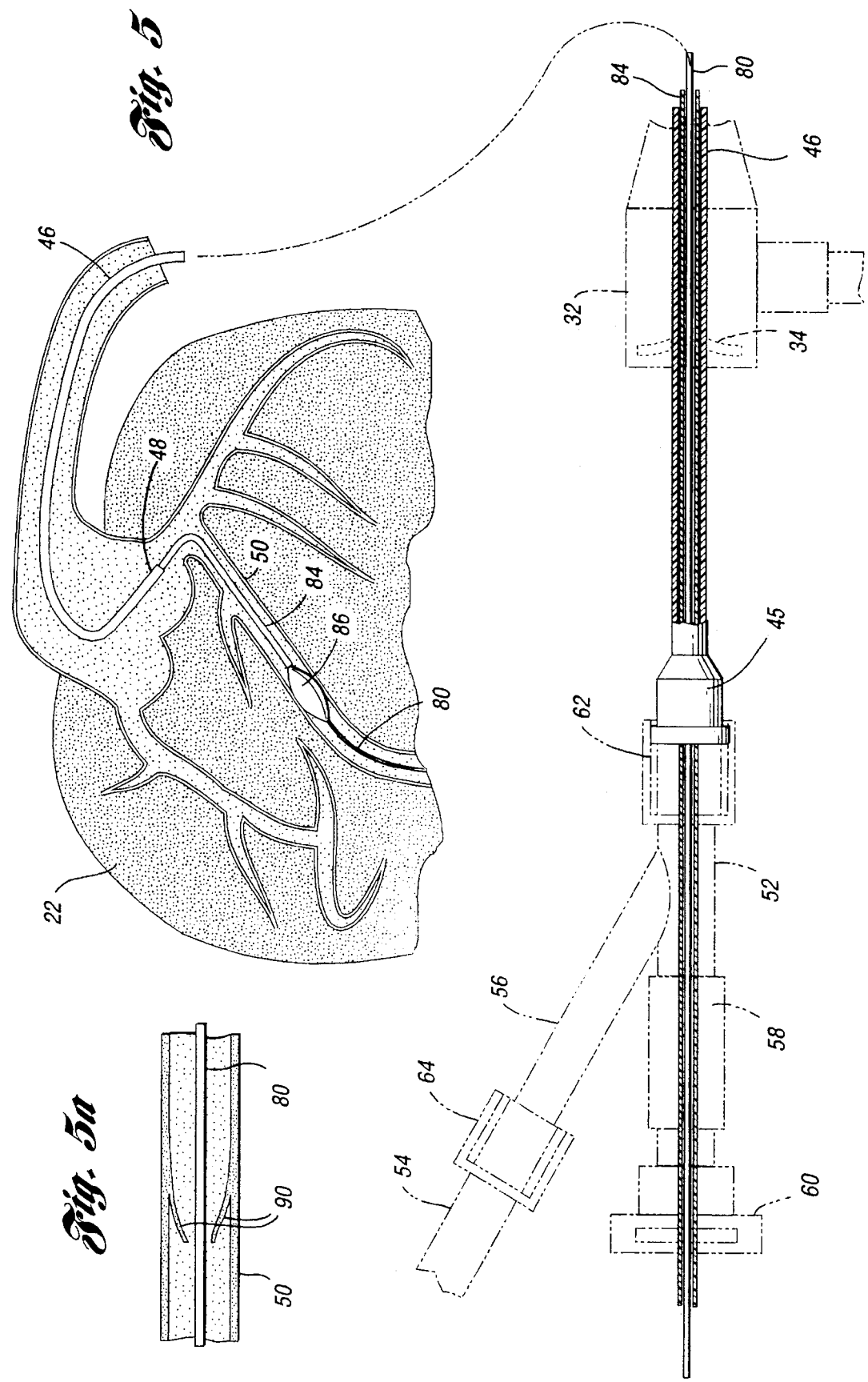
FIG. 5 illustrates the inflation of a balloon at the stenosis.

Once the balloon 86 on the balloon catheter 84 is positioned at the stenosis 81, the balloon is inflated, or repeatedly inflated and deflated, to produce the desired dilation of the lesion and/or distension of the surrounding blood vessel wall. This is shown in FIG. 5. (Similar procedures involve removal of plaque or ultrasound imaging of the artery.)

It is at this point that problems may develop with the angioplasty or related procedures. For example, it is possible that the inner wall of blood vessel 50 could dissect, as shown by reference numeral 90 in FIG. 5A, requiring additional procedures to repair it. In this regard, it is sometimes necessary to resort to open heart surgery to repair such lesions or dissections in the blood vessels.

On the other hand, if the guide catheter system initially used a larger guide catheter, then it might be possible for the cardiologist to repair the problem with a number of other instruments, such as a larger perfusion balloon, an atherectomy device, or a coronary stent. These devices require the use of a larger guide catheter on the order of 8–10 French. Many cardiologists are now hesitant to use a smaller guide catheter system because of the potential problems in exchanging to a larger system. With present systems, if a smaller guide catheter is utilized, such as a 5–8 (preferably 6–7) French guide catheter, it would be difficult to use a perfusion balloon catheter or to place a stent quickly and without potential complications to the patient. The physician would need to completely remove the balloon catheter 84 and more importantly the coronary guide wire 80 from the coronary artery and pull out the smaller introductory sheath 32. This might have the potential to allow the coronary artery to occlude. It thus is desirable not to remove the coronary guide wire 80 since it in large part keeps the coronary artery open and keeps blood flowing down the coronary artery into the myocardium.

If under current procedures, the smaller guide catheter system has to be replaced with a larger guide catheter system, then the smaller system first has to be completely removed from the femoral artery before a larger system can be installed in its place. The exchange procedure involves positioning a 9 or 10 French introductory sheath in the artery and then inserting a larger French guide catheter through the artery and placing it at the desired arterial opening of the heart. More critically, a flexible coronary wire would again have to be positioned through the stenosis, which may be difficult in a dissected artery.

Due to the difficulties in exchanging from a small guide catheter system to a larger guide catheter system, many cardiologists simply use the larger guide catheter system for their procedures. These larger systems allow more flexibility relative to placement of larger perfusion balloons or coronary stents, but increase the risk of hemorrhage around the groin and increase patient morbidity. Smaller guide catheter systems allow for quicker ambulation, potentially shorten the length of hospital stay, provide for a decrease in contrast usage and a decrease in the likelihood of a vascular complication, and also may lower the cost for angioplasty.

The present invention allows use of the smaller guide catheter system for angioplasty, but with the ability to quickly and easily change to a larger guide catheter system without the problems and complications associated with known exchanges. Embodiments of the present invention and procedures for use thereof are shown in FIGS. 6–17.

With the present invention, a guide catheter extender member 100 is used. The extender guide catheter member is attached to the proximal end 47 of the guide catheter 46 in the artery in order to permit exchange of a larger guide catheter system for the smaller guide catheter system. The luer fitting 45 on the proximal end of the implanted guide catheter 46 is removed in order to facilitate use of the extender guide catheter.

Figure 13:
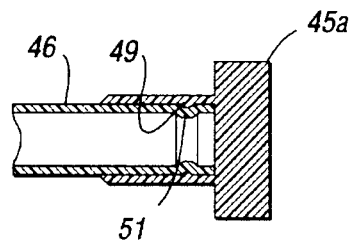
FIGS. 13–16 illustrate alternate embodiments for a detachable hub on the guide catheter.

The luer fitting 45 could be removed simply by cutting or excising the catheter adjacent the fitting. Preferably, however, the hub 45 is detachable or removable from the catheter without the need to cut it off. Some alternative mechanisms to accomplish this are shown in FIGS. 13–16. In FIG. 13, the hub 45a has an internal annular ridge 49 which mates with an annular groove 51 formed adjacent the end of the catheter. When it is desired to remove the hub, it is simply pulled off, either manually or with a special tool.

Figure 14:
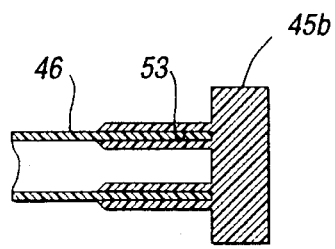

In FIG. 14, the hub 45b has an annular channel 53 which tightly fits over the open end of catheter 46. Again, the hub can be removed manually or with a special tool, depending on the tightness of the fit between the hub and catheter.

Figure 15:
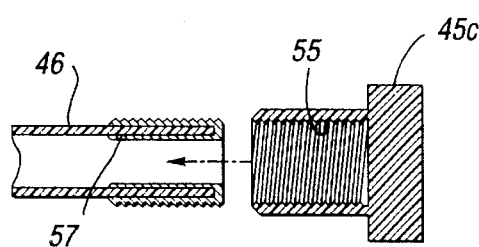
Figure 16:
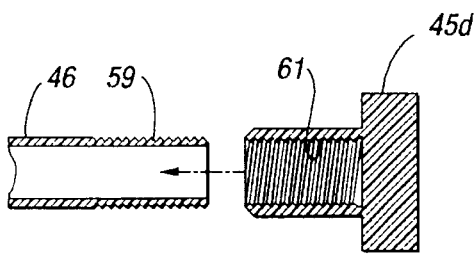

FIGS. 15 and 16 show alternate ways to provide a "screw-on" hub. In FIG. 15, the hub 45c has a threaded internal opening 55. A thin cap member 57 is affixed to the end of the guide catheter 46 and the cap member 57 has a threaded outer surface. In FIG. 16, the end of the catheter 46 has threads 59 formed on its outer circumference which mate with corresponding threads 61 on hub 45d. With the embodiments shown in FIGS. 15 and 16, the hubs 45c and 45d can be screwed onto and off from the guide catheter 46 as needed.

Figure 6:
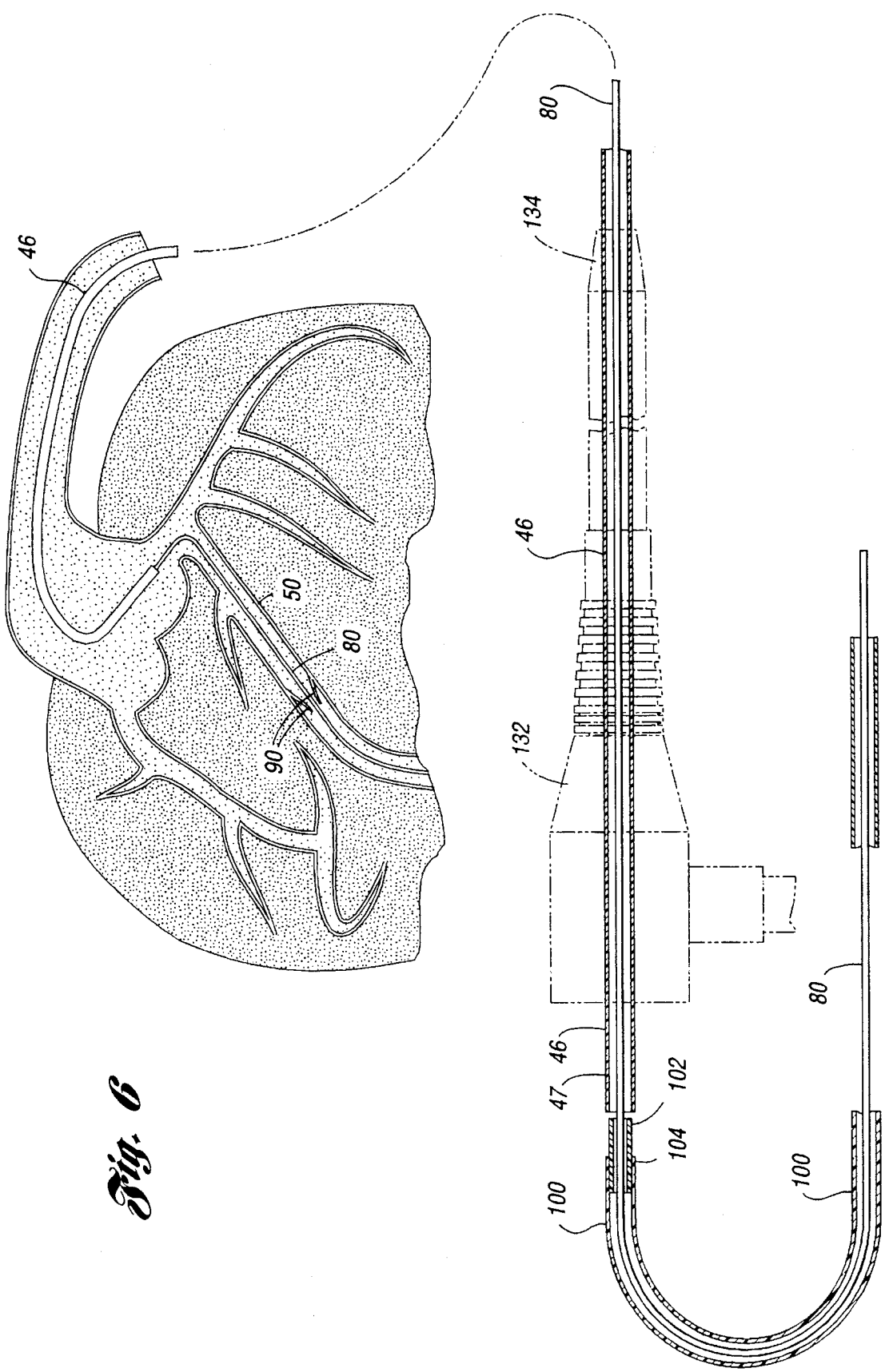
FIG. 6 illustrates the use of a larger introducer sheath and an extender guide catheter in accordance with the present invention.

A connector member 102 is used to join the guide catheter extender member 100 to the guide catheter 46 which is implanted in position in the patient 20. In one embodiment, the connector device 102 is a small tube affixed to the end 104 of the guide catheter extender member 100 and which is forcibly inserted when necessary into the end of the implanted guide catheter member 46. This is shown in FIG. 6. The connector device can be held in place in the implanted guide catheter simply by friction, or the connector device can be threaded or knurled, or otherwise have some variation in cross section in order to help secure it in place in the guide catheter. A threaded connector member 102' is shown, for example, in FIG. 9. It is also possible for the end 47 of the guide catheter 46 to be threaded and for the connector device 102' to have matching threads 106 on it, so that the extender guide catheter member can be screwed onto the implanted guide catheter in order to provide a secure joint and connection. The inside of end 104 of extended guide catheter member 100 can also be threaded.

The particular manner in which the extender member 100 is secured or otherwise attached to the implanted guide catheter 46 is not critical in accordance with the present invention. It is only necessary for the extender 100 and catheter 46 to be attached or connected together in some manner to prevent separation when the larger guide catheter member is implanted in the patient over the smaller guide catheter and extender member. For example, the extender member could be directly attached to the guide catheter 46 without the use of separate connector member. In this regard, the distal end of the extender member could be inserted in or positioned over the proximal end of the guide catheter.

Figure 10:
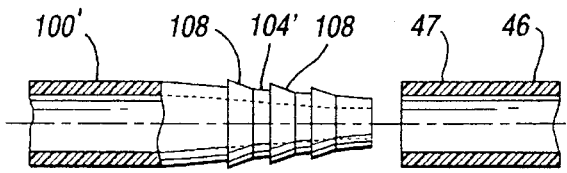

One embodiment for directly connecting the extender catheter guide member to the guide catheter is shown in FIG. 10. The extender member 100' has a tapered end 104' with a plurality of locking tangs or ridges 108 thereon. The ridges 108 securely join the extender member 100' to the guide catheter 46 when end 104' is inserted in end 47. Other ways to directly connect the two catheter tubes together could be utilized.

Also, it is preferred that the joint between the exchanger guide catheter member 100 and the implanted guide catheter member 46 be as flush or smooth as possible. This will allow the larger guide catheter to be inserted in the patient more quickly, and also prevents the larger guide catheter member from causing separation of the two smaller guide catheter members when it is inserted over the joint.

Figure 17:
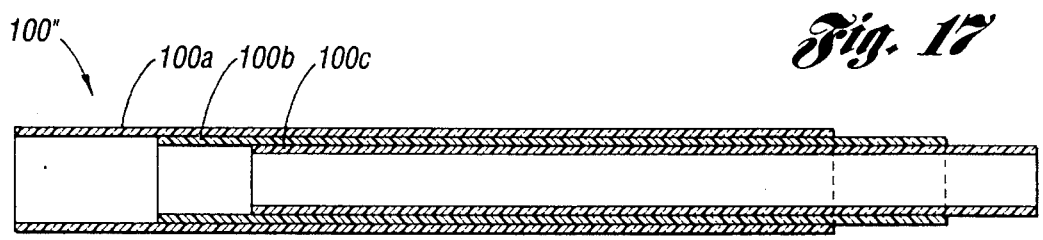
FIG. 17 depicts a telescopic extender guide catheter.

It is also possible to provide a guide catheter extender member which can be expanded or shortened as necessary in order to facilitate its usage in accordance with the present invention. For example, as shown in FIG. 17, the extender member 100" can be comprised of several telescoping shorter catheter members 100*a*, 100*b* and 100*c* which fit inside one another. Member 100" can be extended to the required or necessary length as desired.

In order to use the present guide catheter exchange system, a small guide catheter system (on the order of 5-8 French) is used to initially repair the stenosis or other problem in the patient's artery. The known procedure for doing this is described above with reference to FIGS. 1–5A.

If a problem develops (such as lesion 90, as shown in FIG. 5A), or it is otherwise desired to exchange the smaller guide catheter system with a larger guide catheter system, then the balloon catheter 84 is removed as well as the manifold 54 and hub 52. (It is also possible, but not-preferred, to leave the balloon catheter in place at this point. In this regard, if the balloon catheter is left in place, it also would have to be extended with an extender member in a manner similar to that described above with reference to member 100.)

The original introducer sheath 32 is then removed from the patient and a larger (8–10 French) introducer sheath 132 is positioned in the artery of the patient. Preferably, the distal end 134 of the larger introducer sheath 132 is tapered in order to provide a close fit over the smaller guide catheter member 46 and to prevent leakage of blood and other fluids from the artery. See FIG. 6.

The larger introducer sheath 132 can be substituted for the smaller introducer sheath before or after the extender guide catheter member 100 is attached to the implanted guide catheter member 46. Preferably, however, the introducer sheaths are exchanged before the extender member is attached.

It is preferable that the coronary guide wire 80 currently positioned in place in the patient have sufficient length at its proximal end to protrude beyond the extender guide member. For example, if a 300 cm guide wire 80 is initially utilized, then it will have sufficient length to extend past the extender guide catheter member 100. If a smaller guide wire 80 is utilized, however, which typically are about 150–175 cm in length, then it should first be extended to about 300 cm with a conventional guide wire extender member.

Figure 7:
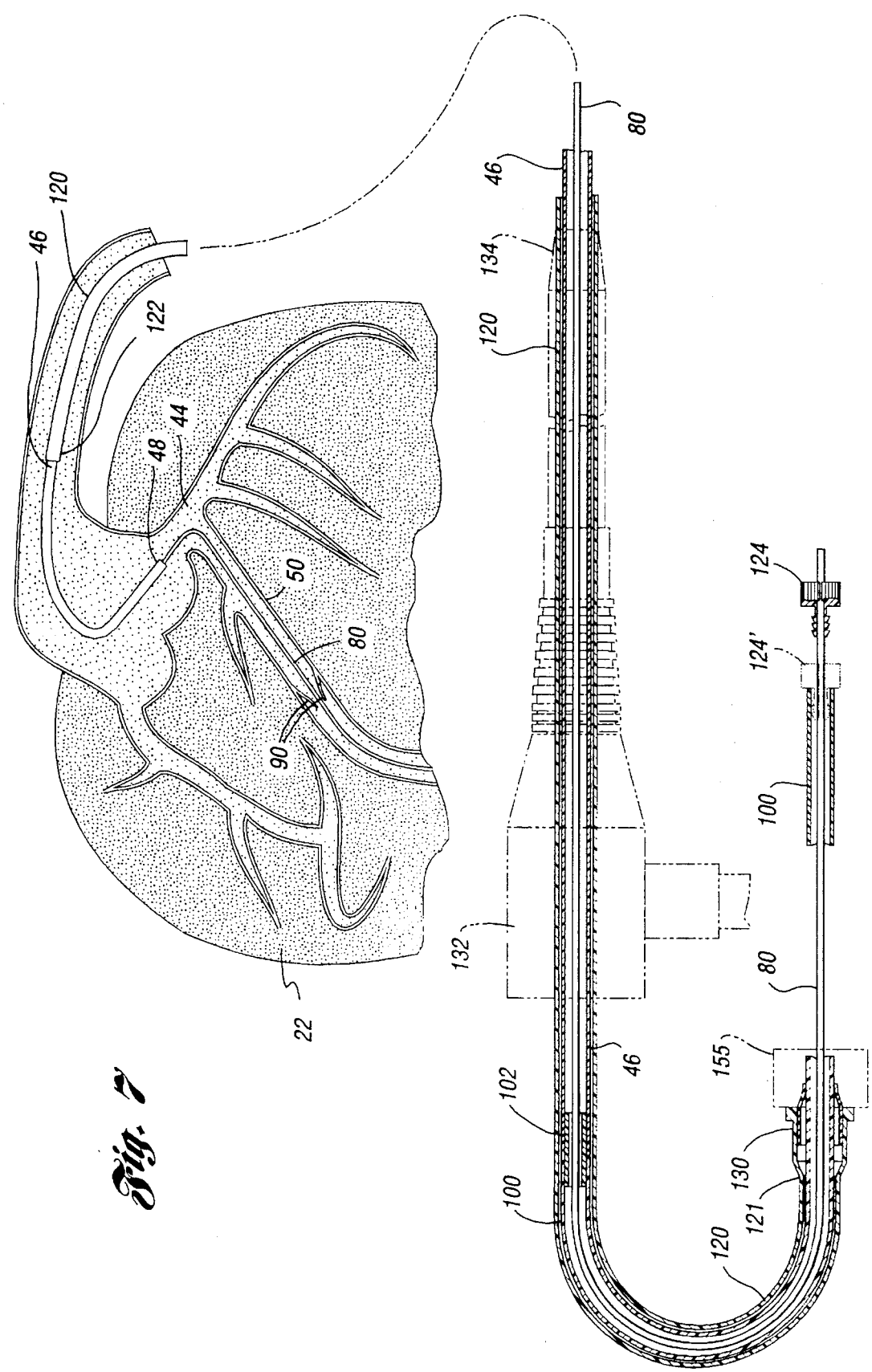
FIG. 7 illustrates the replacement of a small guide catheter with a larger guide catheter in accordance with the present invention.

Once the guide catheter extender member is attached in one of the manners discussed above, a larger (8–10 French) guide catheter 120 is inserted over the smaller and now extended guide catheter 46, 100. This is shown in FIG. 7. The larger guide catheter 120 is advanced until its distal end 122 is positioned at or near the opening of the artery 44, that is, at or near the end 48 of the smaller guide catheter 46. The larger guide catheter is placed over the smaller guide catheter while the smaller guide catheter is still in the aorta slightly removed or still into the coronary artery. It is also possible to remove or begin removal of the smaller guide catheter 46 at the same time that the larger guide catheter 120 is being advanced over it.

For Judkins left guides, the left Judkins curves might need to be relaxed and made more slightly C-shaped in order to allow for ease of exchangeability over standard left Judkins catheters. Right Judkins catheters probably need no modifications.

Since coronary guide wire 80 is still positioned in the coronary artery, a small plug 124 (or wire turner) can be used in order to occlude the proximal end of the extender member 100. See FIG. 7. The plug 124 fits over the wire 80 and is positioned at 124' adjacent the end of the member 100. The plug is then moved simultaneously down the guide wire with the catheter 100 to prevent leakage of fluids from the catheters 46, 100 during and after the attachment of the extender guide catheter member. This would allow for minimal blood loss during the guide catheter exchange which is a problem with current angioplasty guide catheter exchanges.

Figure 8:
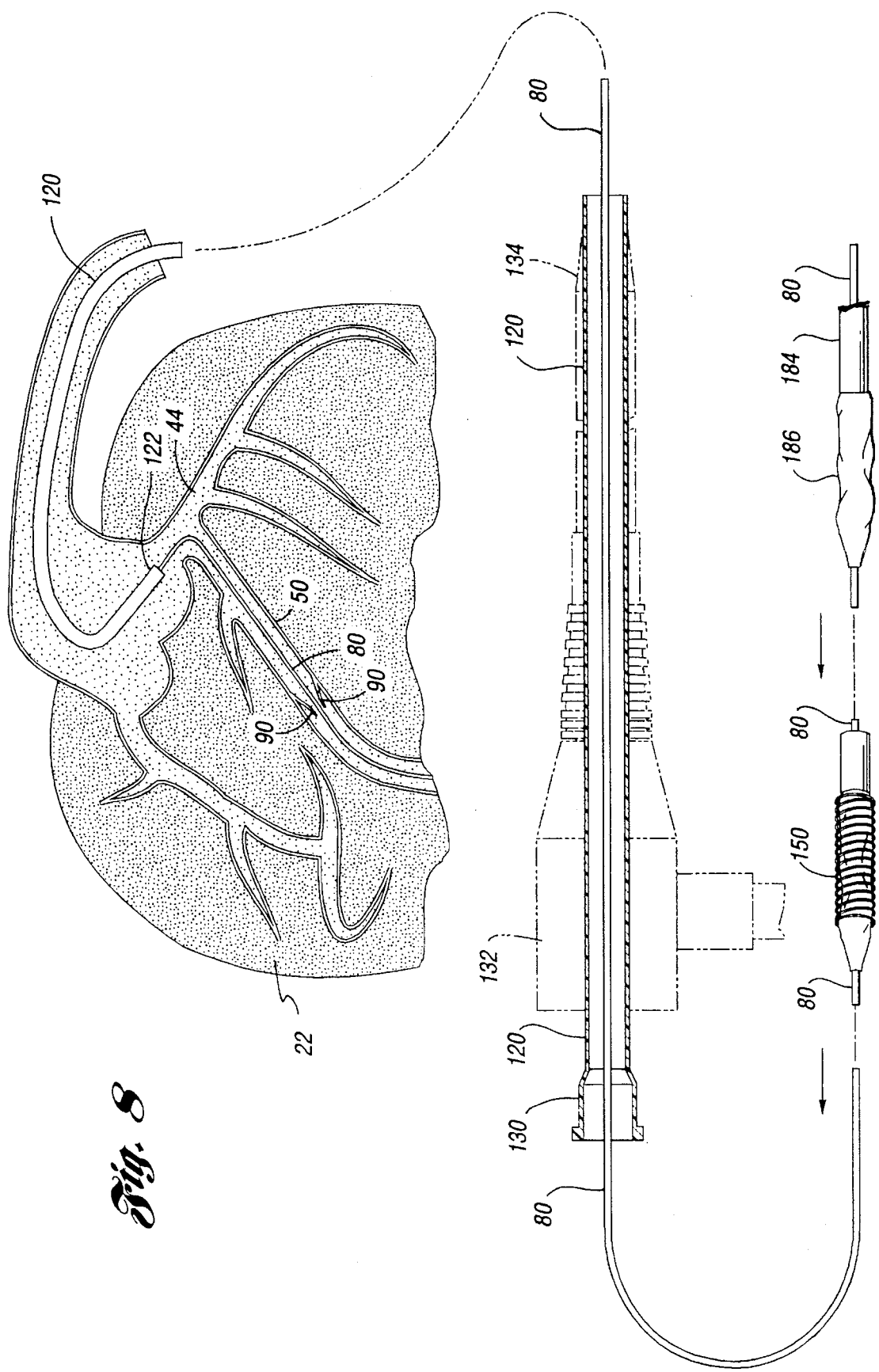
FIG. 8 illustrates the repair of a stenotic lesion with use of the present invention.
Figure 9:
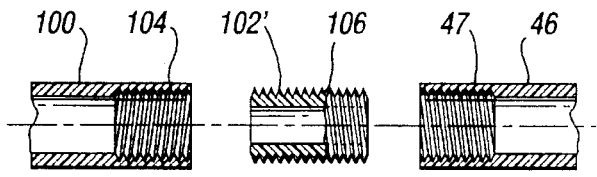
FIGS. 9 and 10 illustrate alternate embodiments of the present invention.

Once the larger guide catheter member 120 is installed in place, as shown in FIG. 8, the smaller guide catheter 46 is removed. It is also possible to begin removal of the smaller guide catheter at the same time that the larger guide catheter is being advanced into position.

It is also desirable to plug or occlude the proximal end 121 of the larger guide catheter 120 in order to prevent leakage of blood from the patient, particularly when the smaller guide catheter 46 and extender catheter member 100 are finally removed. For this purpose, plug 155 is provided. The plug 155 is hollow with a flexible diaphragm 157 to occlude the fluid flow, a slot 159 to fit the plug over the wire 80 and extender member 100, and a pair of flanges 161 to manually secure the plug in the end of the fitting 130. Other types of hemostatic devices, such as a toohey fitting could be used to limit the blood loss.

It is also possible for the exchange of guide catheters to be accomplished with the balloon catheter 84 still in position in the coronary artery. This is done when it is desirable to retain the balloon catheter in the coronary artery, whether to aid in support, or to continue perfusion during the guide catheter exchange. If so, then a detachable hub (not shown) should be positioned on the angioplasty catheter 46 in order to allow a more compatible system.

Once the smaller guide catheter 46 is removed and the larger guide catheter 120 is installed in place, then the cardiologist can utilize the larger guide catheter for the desired repair operation. First the hub 52 and manifold 54 are attached to the luer fitting 130 on the catheter 120. Then the repair procedure could include the placement and use of a larger perfusion balloon 186 as shown in FIG. 8. The larger perfusion balloon catheter 184 is advanced to position over the coronary guide wire 80 and utilized in order to bring about the desired dilation of the offending lesion. Also, the larger guide catheter 120 could be used to facilitate the position of a coronary stent 150 as desired and needed. Other procedures, such as the use of atherectomy devices, rotoblaters or sophisticated imaging or clot dissolving devices or their equivalents could be utilized if desired.

Figure 11:
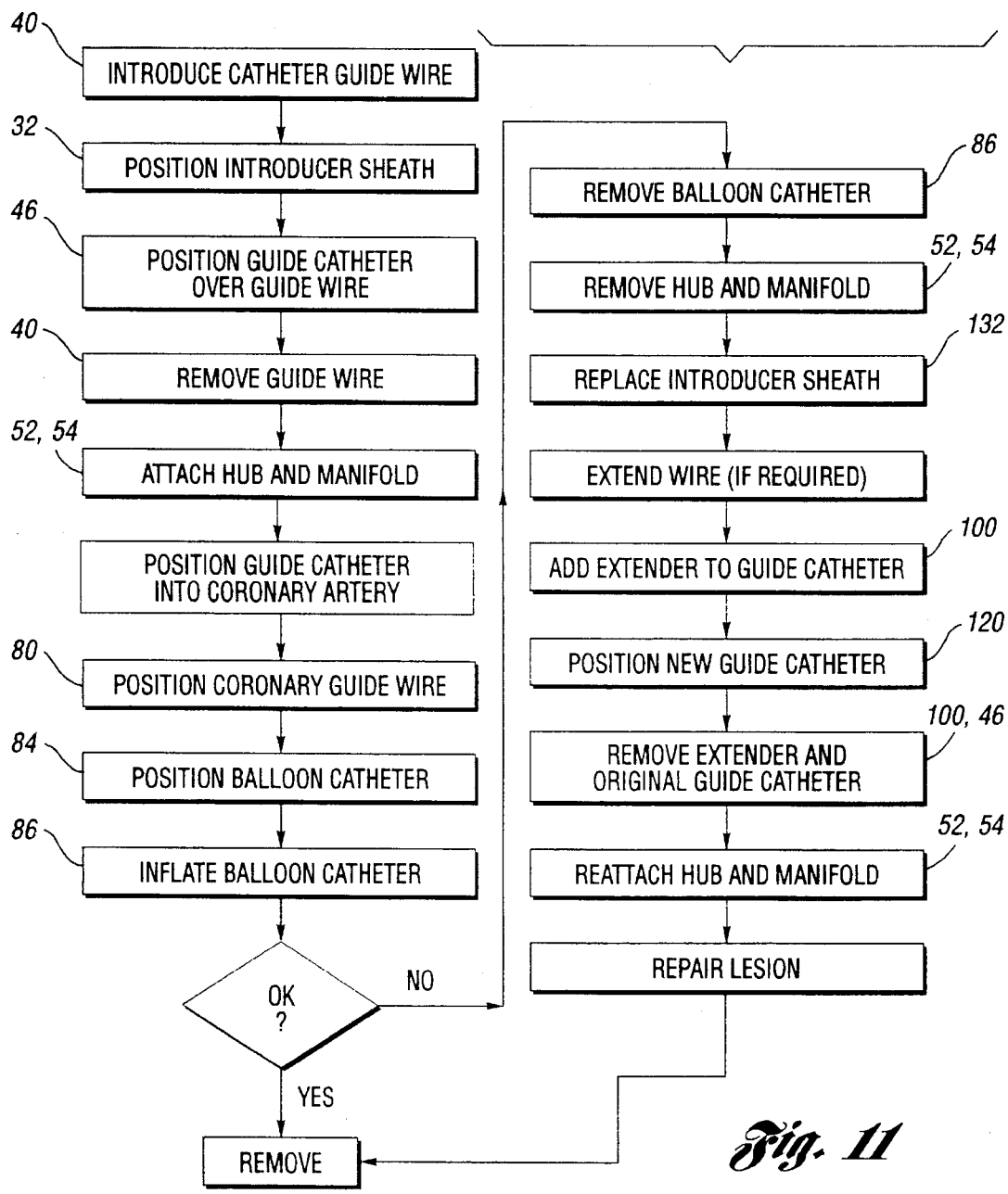
FIG. 11 is a flow chart illustrating the principal steps in accordance with the present invention.
Figure 12:
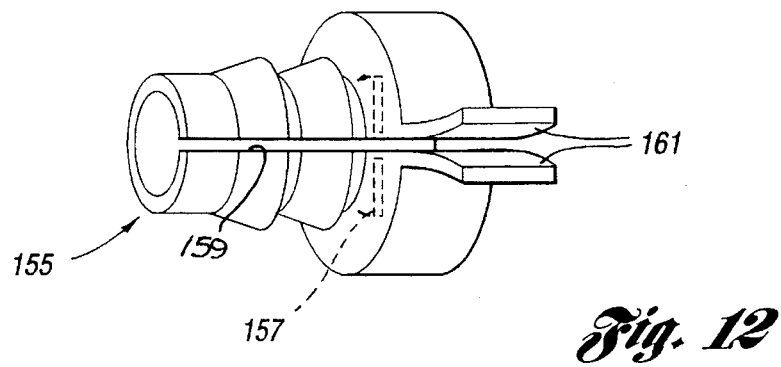
FIG. 12 illustrates a plug or occluder for the larger guide catheter.

A flow diagram setting forth the steps and procedures for use with the present invention is shown in FIG. 11. The reference numerals on the various processing steps correspond to the instruments and devices described above.

The present invention allows the physician increased flexibility with respect to interventional procedures. Although physicians today have flexibility with balloon use and balloon wire exchange, the exchange is limited by the size of the guide catheter system utilized.

The present system allows for guide interchange while allowing the safety of the coronary artery to be continually wired between the interchanges. This helps to prevent the coronary artery from occluding. The present invention also allows physicians to utilize smaller guide catheter systems on a more regular basis, which decreases the risk of hemorrhaging or vascular complications around the groin, decreases patient morbidity, allows for quicker ambulation, and may limit expensive contrast usage. This in turn potentially shortens length of hospital stay, and also results in lower costs to the patient.

Although particular embodiments of the present invention have been illustrated in the accompanying drawings and described in the foregoing detailed description, it is to be understood that the present invention is not to be limited to just the embodiments disclosed, but that they are capable of numerous rearrangements, modifications and substitutions without departing from the scope of the claims hereafter.

What is claimed is:

1. A method of exchanging a first guide catheter system with a second guide catheter system during coronary angioplasty of a patient, said first guide catheter system comprising a first guide catheter, said first guide catheter having a distal end and defining a lumen, said method comprises the steps of:

providing a guide wire having a proximal end and a distal end, positioning the guide wire within the lumen of the first guide catheter;

positioning the first guide catheter within the patient with the distal end of said guidewire being adjacent to the vessel of interest;

advancing an extender guide catheter member over the proximal end of said guide wire;

attaching said extender guide catheter member to said first guide catheter;

inserting a second guide catheter having a distal end over said extender guide catheter member and first guide catheter;

advancing said second guide catheter to a point at which the distal end of said second guide catheter is adjacent to the distal end of said first guide catheter while captivating said guide wire such that the distal end of the guide wire remains adjacent to the vessel of interest;

removing said first guide catheter and extender guide catheter member.

2. The method of claim 1 in which said first guide catheter system further comprises a first introducer sheath and said method further comprises the step of replacing said first introducer sheath with a second introducer sheath.

3. The method of claim 1 wherein said guide wire has a plug thereon for preventing blood and other fluids passing through said extender guide catheter member.

4. The method of claim 1 wherein said first guide catheter has a distal end positioned in said patient and a proximal end positioned exterior of said patient, and said extender guide catheter member is attached to said proximal end.

5. The method of claim 1 wherein said extender guide catheter member is attached to said first guide catheter with a connector device.

6. The method of claim 5 wherein said connector device comprises a tubular member positioned inside said extender guide catheter member and inside said first guide catheter.

7. The method of claim 1 further comprising the step of extending the length of said guide wire prior to attachment of said extender guide catheter member to said first guide catheter.

8. The method of claim 1 wherein said first guide catheter has a diameter of about 6–8 French and said second guide catheter has a diameter of about 8–10 French.

9. The method of claim 2 wherein said second introducer sheath has a distal end and a proximal end, and said distal end is tapered.

10. The method of claim 1 wherein said first guide catheter system further comprises a balloon catheter member, said balloon catheter member having an inflatable balloon.

11. A system for exchanging a first smaller guide catheter member with a second larger guide catheter member, said system comprising an extendable guide catheter member having substantially the same outside diameter as said first guide catheter member, and connector means for detachably connecting said extender guide catheter member to said first guide catheter member.

12. The system as set forth in claim 11 further comprising an introducer sheath.

13. The system as set forth in claim 11 wherein said connector means comprises a tubular member inserted in one end of said extender guide catheter member.

14. The system as set forth in claim 11 wherein said connector means comprises a reduced diameter proximal end on said extender guide catheter member.

15. A method of exchanging a first guide catheter system with a second guide catheter system during coronary angioplasty of a patient, the first guide catheter system comprising a first guide catheter and a first introducer sheath, the first guide catheter having a proximal end, a distal end, and defining a lumen, and the first introducer sheath defining a lumen, the method comprising the steps of:

providing a guide wire having a proximal end and a distal end;

positioning the guide wire within the lumen of the first guide catheter;

positioning the first guide catheter within the lumen of the first introducer sheath;

positioning the first guide catheter system within the patient with the distal end of the guidewire being adjacent to the vessel of interest;

providing an extender guide catheter member having a proximal end and a distal end;

advancing the extender guide catheter member over the proximal end of the guide wire;

attaching the distal end of the extender guide catheter member to the proximal end of the first guide catheter;

removing the first introducer sheath;

providing a second introducer sheath, the second introducer sheath defining a lumen;

advancing the second introducer sheath over the proximal end of the extender guide catheter member;

positioning the second introducer sheath within the patient;

inserting a second guide catheter having a distal end over the extender guide catheter and first guide catheter and inserting the second guide catheter through the lumen of the second introducer sheath;

advancing the second guide catheter to a point at which the distal end of the second guide catheter is adjacent to the distal end of the first guide catheter while captivating the guide wire such that the distal end of the guide wire remains adjacent to the vessel of interest; and removing the first guide catheter and extender guide catheter.

16. The method of claim 15 wherein the guide wire has a plug thereon for preventing blood flow from passing through the extender guide catheter member.

17. The method of claim 15 wherein the extender guide catheter member is attached to the first guide catheter with a connector device.

18. The method of claim 17 wherein the connector device comprises a tubular member positioned inside the extender guide catheter member and inside the first guide catheter.

19. The method of claim 15 further comprising the step of extending the length of the guide wire prior to attachment of the extender guide catheter member to the first guide catheter.

20. The method of claim 15 wherein the first guide catheter has a diameter of about 6–8 French and the second guide catheter has a diameter of about 8–10 French.

21. The method of claim 15 wherein the second introducer sheath has a distal end and a proximal end, and said distal end is tapered.

22. The method of claim 15 wherein said first guide catheter system further comprises a balloon catheter member, said balloon catheter member having an inflatable balloon.

* * * * *